United States Patent
Olcott et al.

(10) Patent No.: US 9,320,478 B2
(45) Date of Patent: Apr. 26, 2016

(54) DUAL-ISOTOPE POSITION EMITTING TOMOGRAPHY FOR DISEASE EVALUATION

(75) Inventors: Peter D. Olcott, Stanford, CA (US); Craig S. Levin, Palo Alto, CA (US); Sanjiv Sam Gambhir, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/113,142

(22) PCT Filed: Apr. 30, 2012

(86) PCT No.: PCT/US2012/035846
§ 371 (c)(1),
(2), (4) Date: Oct. 21, 2013

(87) PCT Pub. No.: WO2012/149552
PCT Pub. Date: Nov. 1, 2012

(65) Prior Publication Data
US 2014/0046179 A1      Feb. 13, 2014

Related U.S. Application Data

(60) Provisional application No. 61/518,153, filed on Apr. 29, 2011.

(51) Int. Cl.
*A61B 6/03*     (2006.01)
*A61B 6/00*     (2006.01)

(52) U.S. Cl.
CPC .............. *A61B 6/037* (2013.01); *A61B 6/5235* (2013.01); *A61B 6/508* (2013.01)

(58) Field of Classification Search
CPC ................................ A61B 6/00; A61B 6/037
USPC .................................................. 600/407, 436
See application file for complete search history.

(56) References Cited

U.S. PATENT DOCUMENTS 5,083,026 A    1/1992    Elbaum
5,512,754 A    4/1996    Enos
(Continued)

OTHER PUBLICATIONS

Andreyev et al. (2011). Dual-isotope PET using positron-gamma emitters. Phys. Med. Biol. 56 (2011) 4539-4556.
(Continued)

*Primary Examiner* — Peter Luong
(74) *Attorney, Agent, or Firm* — Lumen Patent Firm (57) ABSTRACT

Simultaneous dual-isotope positron emission tomography (PET) is used to improve disease evaluation. Two distinct molecular probes are simultaneously provided to the imaging target. One of the probes is labeled with a radionuclide that emits positrons to provide double coincidence events in PET. The other probe is labeled with a radionuclide that emits positrons+prompt gammas to provide triple coincidence events in PET. One of the probes is a metabolic probe, and the other probe is a selective probe that includes a ligand or antibody that is biologically responsive to receptor/antigen status. A PET system is employed that can provide simultaneous double coincidence and triple coincidence PET images. The resulting images provide simultaneous metabolic imaging and receptor/antigen imaging. Applications include disease evaluation, such as cancer staging (e.g., for breast cancer, prostate cancer, etc.).

9 Claims, 4 Drawing Sheets

(56) References Cited

U.S. PATENT DOCUMENTS

| | | | |
|---|---|---|---|
| 6,484,051 B1* | 11/2002 | Daniel | 600/436 |
| 7,777,189 B2 | 8/2010 | Schweizer et al. | |
| 2003/0012731 A1* | 1/2003 | Suddarth et al. | 424/1.49 |
| 2008/0033291 A1 | 2/2008 | Rousso et al. | |
| 2008/0283758 A1 | 11/2008 | Hayden et al. | |
| 2009/0057561 A1* | 3/2009 | Schweizer et al. | 250/363.04 |
| 2009/0137909 A1* | 5/2009 | Luiken | 600/476 |
| 2010/0015058 A1 | 1/2010 | Li et al. | |
| 2010/0260673 A1 | 10/2010 | Cao et al. | |
| 2010/0268074 A1 | 10/2010 | Van Loef et al. | |

OTHER PUBLICATIONS

Andreyev et al. (2012). EM Reconstruction of Dual Isotope PET with Staggered Injections and Prompt Gamma Positron Emitters. 2012 IEEE Nuclear Science Symposium and Medical Imaging Conference Record (NSS/MIC), pp. 3701-3706.

Andreyev at al. (2010). Feasibility Study of Dual Isotope PET. 2010 IEEE Nuclear Science Symposium Conference Record, pp. 2108-2111.

Andreyev at al. (2010). Feasibility Study of a Dual-Isotope PET Technique. M07-3: (11:00) (07: New Imaging Techniques, Thursday, Nov. 4 10:30-12:00; in Ballroom B). http://www.nssi mic.org/2010/program/ListProgram.asp?session=M07.

Andreyev et al. (2011). Feasibility study of dual isotope PET. Nuclear Science Symposium Conference Record (NSS/MIC), 2010 IEEE , Issue Date: Oct. 30, 2010-Nov. 6, 2010, pp. 2108-2111.

Miyaoka et al. (2011). Dual-Radioisotope PET Data Acquisition and Analysis. 2011 IEEE Nuclear Science Symposium Conference Record, pp. 3780-3783.

Sitek et al. (2011). Reconstruction of Dual Isotope PET Using Expectation Maximization (EM) Algorithm. 2011 IEEE Nuclear Science Symposium Conference Record, pp. 4323-4326.

* cited by examiner

DUAL-ISOTOPE POSITION EMITTING TOMOGRAPHY FOR DISEASE EVALUATION

CROSS-REFERENCE TO RELATED APPLICATIONS

This application is a 371 of PCT application PCT/US2012/035846 with filing date Apr. 30, 2012. PCT application PCT/US2012/035846 claims the benefit of U.S. Provisional application 61/518,153 with filing date Apr. 29, 2011.

STATEMENT OF GOVERNMENT SPONSORED SUPPORT

This invention was made with Government support under contract no. CA118681 awarded by the National Institutes of Health. The Government has certain rights in this invention.

FIELD OF THE INVENTION

This invention relates to disease evaluation using positron emission tomography (PET).

BACKGROUND

Positron emission tomography is often employed in connection with diagnosis and staging of diseases, such as cancer. In the case of cancer, it is important to evaluate both the primary tumor (if present) and all secondary tumors that may be present due to metastasis during staging. Although the secondary tumors originate from the primary tumor, it is possible for the secondary tumors to differ from the primary tumor (or from each other) in significant ways. For example, the receptor status of secondary tumors may or may not be the same as the corresponding receptor status of the primary tumor. Also the receptor status of the secondary tumors may differ from one secondary tumor to another.

A positron emission tomography system includes an arrangement of many detection units around an imaging subject that can determine the position, energy, and arrival time of incoming high energy photons that result from positron annihilation in the imaging subject. Positron emitting isotopes, such as F-18, can be used to label and track the biodistribution of biologically relevant molecules ("molecular probes" or "contrast agents") throughout the body using a PET system.

It is convenient to classify molecular probes as being metabolic if they relate to cell metabolism in general (without antibody/antigen selectivity) and as being selective if they include an antibody or ligand that is biologically responsive to cell receptor or antigen status.

In a non-limiting example, metabolic probes are usually small molecules in which F-18 has been used for labeling the molecule. For example, FDG (Fludeoxyglucose (18F)) is a small molecule metabolic molecular probe because it is a glucose analog that is taken up by all glucose using cells.

Selective molecular probes can be used in PET imaging to provide images that relate to abnormal expression of proteins, such as HER2/neu (Human Epidermal Growth Factor Receptor 2), which is over-expressed in about 30% of breast cancers.

Another class of small molecule probes relates to functional or physiological parameters. Emitters such as C-11, N-13, or O-15 can be labeled to molecules such as water, oxygen gas, carbon dioxide gas, and ammonia without modifying the structure or behavior of the molecule.

Lastly, there are classes of small molecule probes that are close analogs of neurotransmitters. F18-DOPA is a small molecule example of a neuro-transmitter PET isotope.

It is often useful to obtain both metabolic imaging and selective imaging when evaluating disease. Metabolic PET imaging provides information on total disease burden, while selective PET imaging can be used to determine the applicability of certain kinds of therapy. For example, monoclonal antibody therapy for cancer is appropriate only in cases where the corresponding receptor is present in the primary and/or secondary tumors. Selective PET imaging can be used to image the relevant receptor status of the tumors.

However, in conventional PET, only one positron emitting radionuclide can be imaged at the same time in a given region of interest in the body, even if different molecular probes having distinct radionuclides are used. This is because the different positron emitting radionuclides all emit positrons which annihilate to provide 511 keV annihilation photons that cannot be distinguished from each other by their energy.

Thus, in order to perform both metabolic PET imaging and selective PET imaging, one conventional approach is to perform two imaging runs in succession, with enough time delay between them to allow the labeled molecular probes of the first imaging run to clear (e.g., a time delay greater than several half-lives of the radionuclide used in the first imaging run). Unfortunately, the need for two imaging runs undesirably increases imaging time and cost. Another known approach is to provide two labeled molecular probes simultaneously, and rely on differing half lives of the radionuclides to distinguish the two PET images. However, such approaches require PET data as a function of time (as opposed to a static image), and also relies on significant assumptions relating to in vivo behavior of the labeled molecular probes. Another method requires the two molecular probes (e.g., Na18F and FDG) to have significantly different biodistributions in the body so that they can be spatially separated. However, in this latter approach there is usually significant spillover between the different biodistributions so that they cannot be truly anatomically separated.

Accordingly, it would be an advance in the art to provide improved PET imaging for disease evaluation.

SUMMARY

The present approach alleviates the above-identified problems by utilizing simultaneous dual-isotope PET. Two distinct molecular probes are simultaneously provided to the imaging target. One of the probes is labeled with a radionuclide that emits positrons to provide double coincidence events in PET. The other probe is labeled with a radionuclide that emits positrons+prompt gammas to provide triple coincidence events in PET. One of the probes is a metabolic probe, and the other probe is a selective probe that includes a ligand or antibody that is biologically responsive to receptor/antigen status. A PET system is employed that can provide simultaneous double coincidence and triple coincidence PET images. The resulting images provide simultaneous metabolic imaging and receptor/antigen imaging. Applications include disease evaluation, such as cancer staging (e.g., for breast cancer, prostate cancer, etc.).

This approach provides significant advantages. Simultaneous metabolic PET imaging and selective PET imaging provides imaging results which are automatically spatially registered to each other, and advantageously reduces imaging time (and cost).

DETAILED DESCRIPTION

Figure 1:
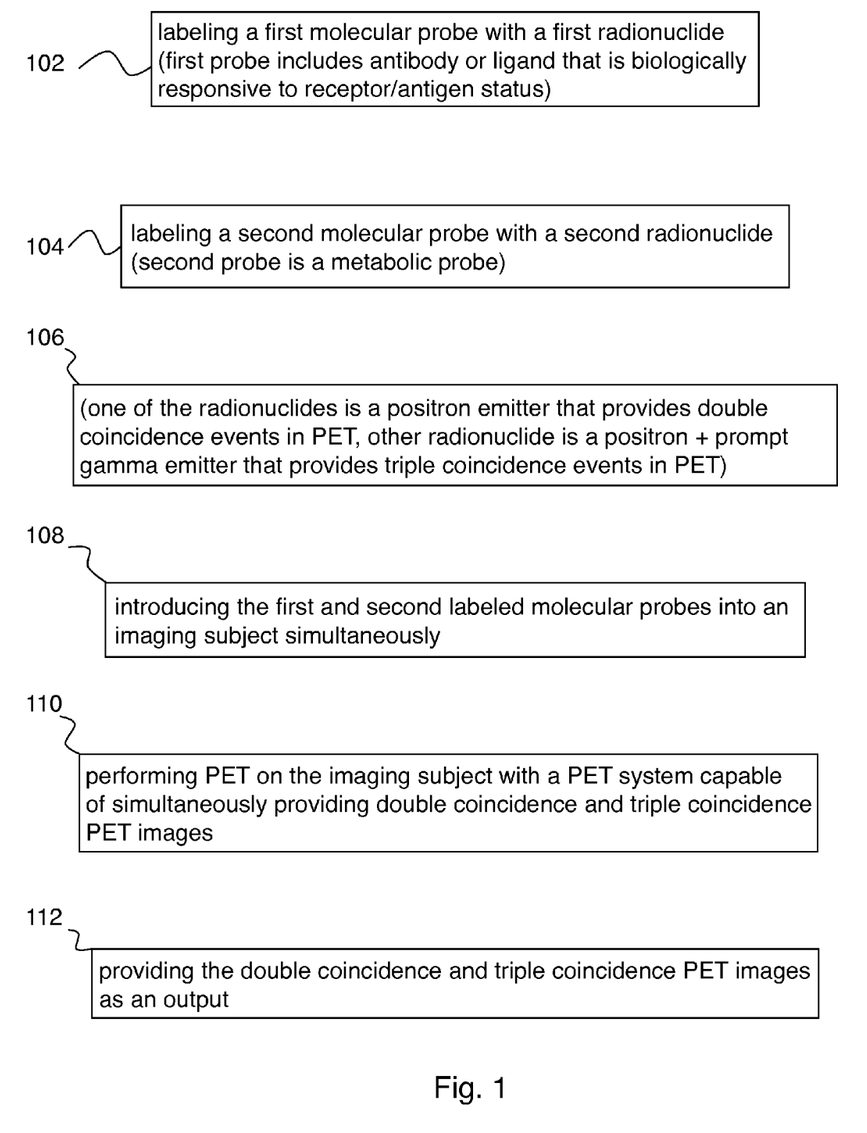
FIG. 1 shows a method for positron emission tomography according to an embodiment of the invention.

FIG. 1 shows a method for positron emitting tomography according to an embodiment of the invention. In step 102, a first molecular probe is labeled with a first radionuclide. The first probe includes an antibody or ligand that is biologically responsive to a receptor or antigen status of cells in the imaging target (i.e., the first probe is a selective probe as defined above). In step 104, a second molecular probe is labeled with a second radionuclide. The second probe is a metabolic probe as defined above. As indicated at 106, one of the radionuclides is a positron emitter that emits positrons to provide double coincidence events in PET, and the other radionuclide is a positron+prompt gamma emitter that provides triple coincidence events in PET. In step 108, the two labeled molecular probes are introduced into an imaging subject simultaneously. The imaging subject can be a human patient, a small animal, or any other PET imaging subject. Imaging of a human patient can be either whole-body or application-specific (e.g., imaging of a single organ or limited region of a patient's body).

In step 110 (described below in greater detail in connection with FIGS. 4 and 5), PET is performed on the imaging subject with a PET system capable of simultaneously providing double coincidence and triple coincidence images. The resulting images are then provided as an output in step 112. Since the two images relate separately to the metabolic and selective probes, simultaneous metabolic and selective PET imaging is thereby provided.

In some embodiments, the first radionuclide is the double coincidence emitter and the second radionuclide is the triple coincidence emitter. In other embodiments, this is reversed (i.e., the first radionuclide is the triple coincidence emitter and the second radionuclide is the double coincidence emitter). In most cases, this second approach is preferred, because the first molecular probe is the selective probe responsive to receptor/antigen status, and the relatively long biological half-life of antibody-antigen binding is consistent with the relatively long physical half-life of typical triple coincidence radionuclides. Suitable triple coincidence radionuclides include, but are not limited to: I-124, In-110, Sc-44, Ga-68, and Na-22. Suitable double coincidence radionuclides include, but are not limited to: F-18, C-11, and Cu-64

Any molecular probe that is biologically responsive to the receptor or antigen status of cells in the imaging subject can be employed as the first probe in the above-described method. In many cases, it is convenient to describe such probes according to the antigen or receptor that they selectively bond to. Thus, any probe that selectively bonds to a receptor or antigen that is over-expressed or under-expressed in a disease can be employed here. Suitable probes include, but are not limited to probes that selectively bond to an antigen or receptor selected from the group consisting of: human epidermal growth factor receptor 2 (HER2/neu), estrogen receptor alpha (ER-α), estrogen receptor beta (ER-β), and prostate-specific membrane antigen (PSMA).

Any molecular probe that is a metabolic probe can be employed as the second probe in the above described method. Preferred metabolic probes include, but are not limited to FDA-approved metabolic probes labeled with F-18, such as Fludeoxyglucose (FDG), 3'-fluoro-3'-deoxy-L-thymidine (FLT), and F-choline.

Figure 2:
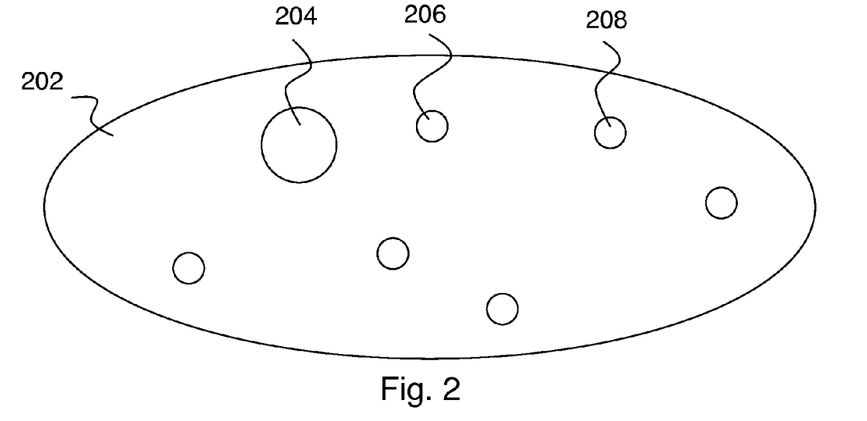
FIG. 2 schematically shows a patient having primary and secondary tumors.
Figure 3A:
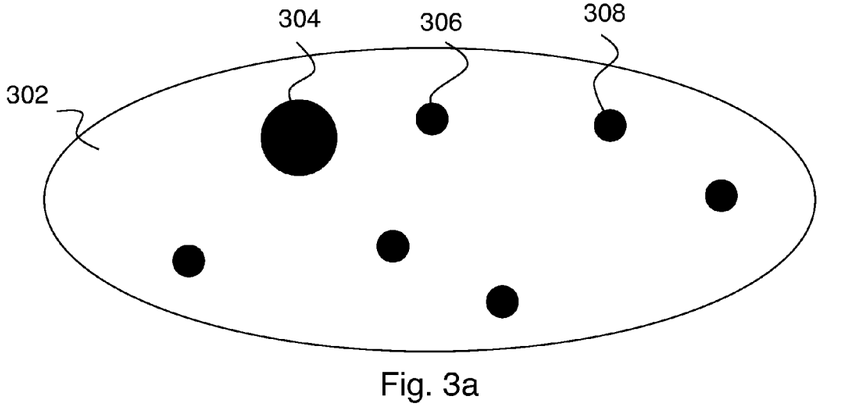
FIGS. 3a-b schematically show dual isotope PET imaging results according to principles of the invention.

FIG. 2 and FIGS. 3a-b schematically show an application of the present principles to cancer staging. FIG. 2 shows a patient 202 having a primary tumor 204 and multiple secondary tumors (e.g., from metastasis). Two of the secondary tumors are referenced as 206 and 208. FIG. 3a schematically shows what one would expect from metabolic PET imaging of the patient of FIG. 2. All of the primary and secondary tumors should be imaged, since they all take up metabolic probes. Thus, primary tumor 204 is imaged as 304, and secondary tumors 206 and 208 are imaged as 306 and 308 respectively. For simplicity, the imaged tumors are all shown with the same shade of black on this figure, even though quantitative data on tumor burden for each tumor location may be obtained by quantitative metabolic PET image analysis.

Figure 3B:
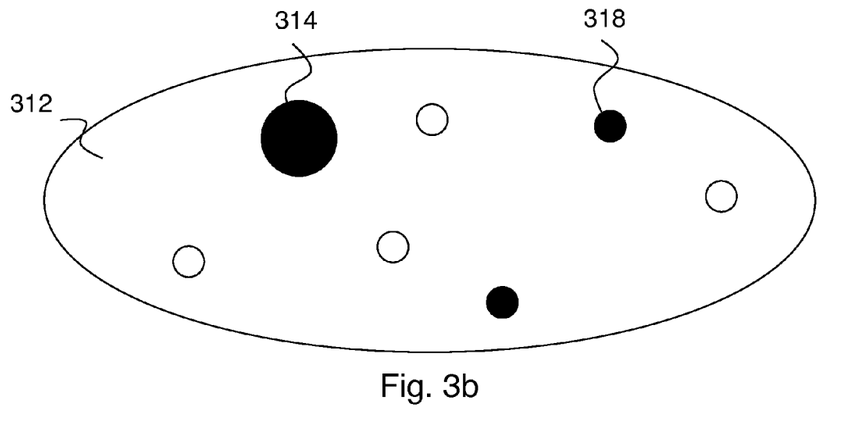

FIG. 3b schematically shows what one would expect from selective PET imaging of the patent of FIG. 2. Some of the primary and secondary tumors should be imaged, since each tumor may or may not take up the selective probes. In this schematic example, primary tumor 204 is imaged as 314, secondary tumor 206 is not imaged, and secondary tumor 208 is imaged as 318. For simplicity, the imaged tumors are all shown with the same shade of black on this figure, even though quantitative data on receptor response for each tumor location may be obtained by quantitative selective PET image analysis.

In this example, the images of FIGS. 3a and 3b would be obtained simultaneously in a single imaging run, and would automatically have proper spatial registration of the two images. As indicated above, this is highly advantageous, since the time taken to acquire the two images can be significantly reduced compared to conventional separate acquisition of the two images.

The molecular probe used for the selective imaging of FIG. 3b is preferably biologically responsive to an antigen or receptor that relates to the cancer being staged. For example, suitable selective probes for breast cancer could bind to HER2/neu, ER-α, or ER-β. Suitable selective probes for prostate cancer could bind to PSMA.

I-124 is a triple coincidence emitter of particular interest for some applications. I-124 has been used to label special ligands and antibodies that are used to assay status of receptors or other markers on the cell surface that are overexpressed in diseased cells. More specifically, I-124 (half-life ~4.2 days) is a positron-emitting radionuclide that displays excellent potential for use in the design and synthesis of radioimmunoconjugates for "immunoPET." Immuno-positron emission tomography (immunoPET) is the tracking and quantification of monoclonal antibodies (mAbs) with PET in vivo (in living subjects), which can improve diagnostic imaging and guide mAb-based therapy. For example, in Sundaresan et al. ("124*I-labeled engineered anti-CEA minibodies and diabodies allow high-contrast, antigen-specific small-animal PET imaging of xenografts in athymic mice", J. Nuclear Medicine*, v44n12, December 2003, pp 1962-1969), I-124 is used to label molecular probes that provide antigen-specific binding for in vivo PET imaging. Analogous molecules and disease states are envisioned, for example breast cancer and Her-2/neu receptor PET imaging as in Dijkers et al. (*Clinical Pharmacology and Therapeutics* v87n5:586-592). I-124 is particularly appealing because its physical half-life is comparable to the biological half-life of antibodies.

The most common probe used in PET cancer imaging is F-18 labeled FDG, a marker for upregulated cellular glycolysis that is common in many types of cancers. Thus, while the bio-distribution of I-124 labeled antibody injected into the body can be imaged to assay, for example receptor status on tumor cells, simultaneously, the bio-distribution of the radiopharmaceutical FDG can be used to assay tumor burden characterized by upregulated glycolysis within the cell.

This ability to perform simultaneous measurement of both cellular receptor status and another feature such as cellular glycolysis status rather than performing two separate studies will create a powerful multiplexing tool to enable more accurate diagnostic imaging and monitoring of antibody-based therapy for disease. While two separate PET studies could give separate information about receptor status and cellular glycolysis status at different time points, due to temporally varying biology and patient/organ motion, the simultaneous acquisition of both parameters will provide superior accuracy, and be less costly and more convenient for both patient and physician (one scan with the two biological assays naturally co-registered spatially and temporally).

In general, this approach can be used with any combination of two radionuclides—one of which is a pure positron emitter that provides double coincidence events, and the other of which is a positron+gamma emitter that provides triple coincidence events. As indicated above, prostate cancer and breast cancer are possible applications, but applications to other diseases that would benefit from more accurate imaging of ligands or antibodies performed simultaneously with measurement of another biological feature of disease such as cellular glycolysis are also possible. Furthermore, the general method also holds for cases of imaging disease states that are characterized by underexpression rather than overexpression of certain receptors.

Figure 4:
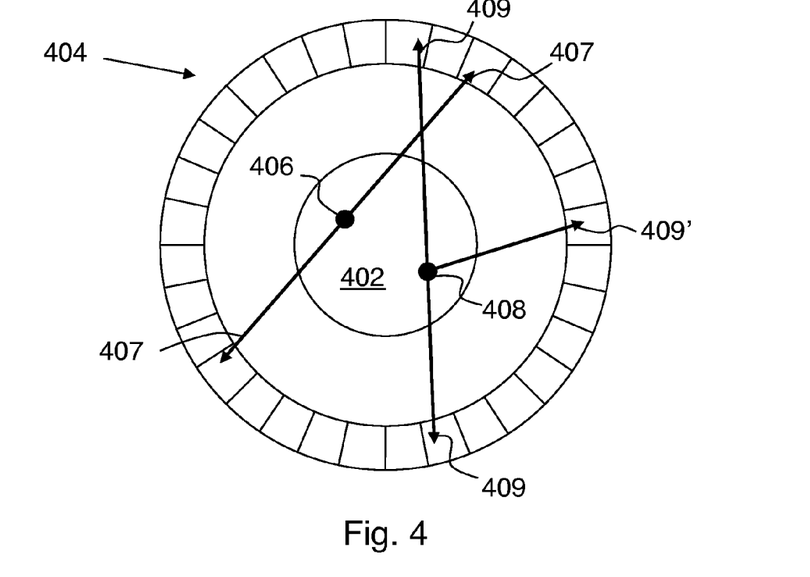
FIG. 4 shows an apparatus suitable for practicing embodiments of the invention.

Some aspects of the present approach can be better appreciated by considering simultaneous dual-isotope PET imaging in greater detail. FIG. 4 shows an apparatus suitable for practicing embodiments of the invention. This apparatus is basically a conventional PET system, where an array of imaging PET detectors 404 surrounds an imaging subject 402. A double coincidence event 406 in subject 402 leads to two oppositely directed 511 keV photons 407 as a result of positron annihilation. Detection of such double coincidence events is the basis for conventional PET. A triple coincidence event 408 in subject 402 leads to two oppositely directed 511 keV photons 409 as a result of positron annihilation, and a third photon 409' (i.e., the prompt gamma of the triple coincidence radionuclide). Triple coincidence events can be distinguished from double coincidence events by the presence of a third detection signal in the relevant time window.

Figure 5:
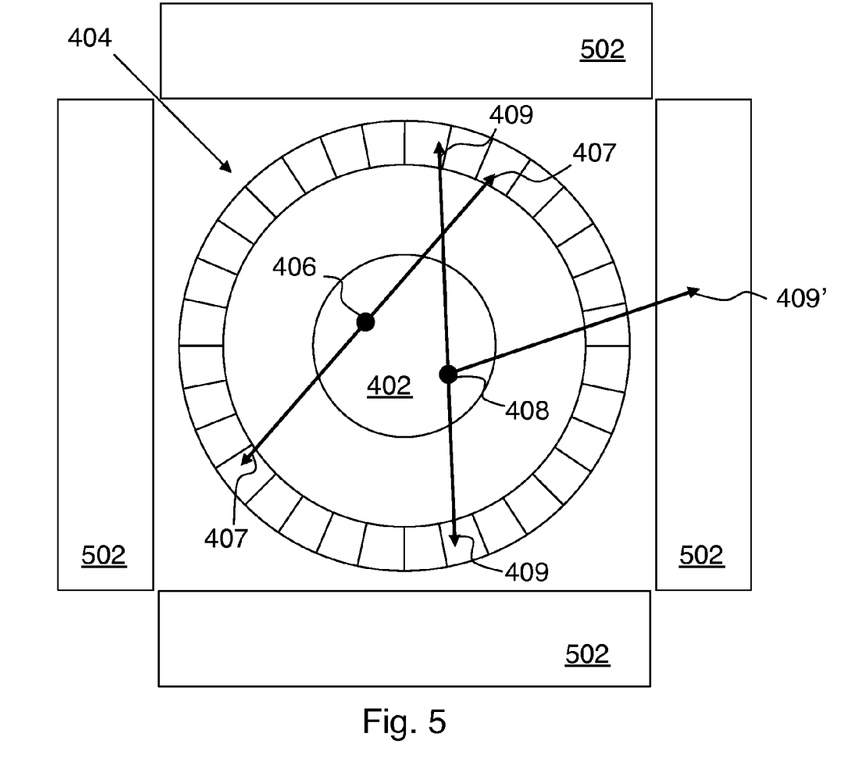
FIG. 5 shows another apparatus suitable for practicing embodiments of the invention.

FIG. 5 shows another apparatus suitable for practicing embodiments of the invention. This apparatus is similar to the apparatus of FIG. 4, except that additional prompt gamma detectors 502 are disposed around the imaging PET detector array 404. Prompt gamma detectors 502 are not responsive to 511 keV photons, and need not provide any significant spatial resolution. These detectors provide a cost-effective way to increase system sensitivity for triple coincidence events, because adding detectors that need not provide significant spatial resolution is relatively inexpensive. Here an event is classified as a triple coincidence event if there is a double coincidence event in detector array 404 combined with detection of a third photon in the relevant time window. This third photon can be detected anywhere in the system (i.e., in any of the additional detectors 502, or in the detector array 404). Spatial resolution for triple coincidence events is provided by the detection of annihilation photons 409 in detector array 404, which is the reason that detectors 502 need not provide spatial resolution.

Further details relating to the preferred approach of FIG. 5 are described in international patent application PCT/US2012/031619, filed on Mar. 30, 2012, entitled "Methods and systems for increasing the sensitivity of simultaneous multi-isotope positron emission tomography", and hereby incorporated by reference in its entirety. As an alternative, by employing certain system software and firmware modifications, conventional PET systems (e.g., as in FIG. 4) can also be adapted to distinguish double coincidences from triple coincidences. However, such modified conventional PET systems may undesirably have a much lower triple coincidence photon detection efficiency than the systems described in PCT/US2012/031619.

Some further aspects of triple coincidence detection as considered in PCT/US2012/031619 are reproduced in the following paragraphs, for completeness.

Typically, prompt gamma detectors 502 are energy selective in order to be responsive to the prompt gammas without being responsive to the 511 keV annihilation photons. Thus, these detectors have an energy window within which they respond, thereby providing energy selectivity. The energy window can be based on the energy resolving capability of the detector. The prompt gamma energy can be greater than 511 keV or less than 511 keV. For a detector with a good energy resolving capability, the selected energy window can be +/−10% of the prompt gamma ray energy. The energy window can also be made wider than +/−10% to improve sensitivity. For example, suppose the prompt gamma has an energy of 800 keV. The above described 10% rule would give an energy window of 720 to 880 keV. The lower end of this window can be decreased (e.g., to 600 keV). A 600-880 keV window will increase the sensitivity of the detector because a Compton interaction that deposits some of the energy of the prompt gamma ray can be as or more likely than ionization that deposits all of the energy of the prompt gamma ray. Thus, it can be helpful to decrease the lower limit of the energy window (while continuing to exclude 511 keV from the window) because some detection events for the prompt gamma will not have the full energy of the prompt gamma. The preceding examples relate to use of an energy window for providing responsiveness to prompt gammas and non-responsiveness to 511 keV annihilation photons. Any other method for providing this selective response capability can also be employed.

Another non-limiting example of a method to determine if a gamma photon is prompt is to use a time window. Because the approximate location of an annihilation event is known by the time-of-flight of the 511 keV annihilation photons, then correspondingly, the time of flight of a potential third gamma can be calculated. If the third gamma is within an acceptable time of flight from the annihilation location, then this can be used to determine whether or not the third gamma is prompt.

PET detector signals can be classified as 2-photon events or as 3-photon events according to signals provided by the PET detector array 404 and by the prompt gamma detectors 502. For example, PET analysis of the signals from detector array 404 can provide a list of positron annihilation events. Each of these annihilation events can be classified as a 2-photon event or as a 3-photon event according to the absence or presence, respectively, of a third coincident detector signal from the prompt gamma detectors 502 or from the PET detector array 404. In either case, detection of the prompt gamma ray does not need to be spatially localized. The localization of the positron decay is done by the localization of the two annihilation photons 407 (or 409) based on energy discrimination and time discrimination.

In most cases, it is preferred for PET detector array 404 to laterally enclose the object being imaged. In other words, the PET detector array has generally the configuration of the side surface of a cylinder that is disposed around the object being imaged. It is also preferred for the PET detector array to provide a spatial resolution substantially more precise than the size of the PET detector array. Methods for accomplishing this are well known in the art relating to PET. Any and all such methods are applicable here.

As indicated above, it is preferred for the prompt gamma detectors to not provide a spatial resolution more precise than their size. This configuration is preferred to minimize the added cost of the prompt gamma detectors. Of course, prompt gamma detectors providing spatial resolution more precise than their size can be employed, but that would increase cost without providing any significant benefit.

As previously described, 2-photon and 3-photon events are distinguished by the absence or presence of a third detector signal that is coincident with a 2 photon coincidence event as recorded in PET detector array 404. A timing window is employed to determine whether or not such a coincidence has occurred, since exact coincidence is not expected in practice. These timing considerations also affect the desired properties of the prompt gamma emitters.

For whole body PET systems, let w be the patient width, and let c be the speed of light. Then we define $\tau=w/c$. Preferably, the triple-coincidence isotope has a time difference T between positron emission and prompt gamma emission such that T is less than about $\tau$. Note that the prompt gamma can be emitted before or after the positron, so T is by convention defined as a positive quantity (i.e., $T=|t_{pos}-t_{gam}|$, for a prompt gamma emitted at time $t_{gam}$ and a positron emitted at $t_{pos}$). For this case, the coincidence window for defining 3-photon events is preferably in a range from 0 to W, where W is between about $\tau$ and about $3\tau$.

For small animal and application-specific PET systems, let $T_{FWHM}$ be the detector time response full width half-maximum. Preferably, the triple-coincidence isotope has a time difference T between positron emission and prompt gamma emission such that T is less than about $2T_{FWHM}$. For this case, the coincidence window for defining 3-photon events is preferably in a range from 0 to W, where W is about $2T_{FWHM}$.

In some cases, such as low-count rate situations (as often encountered in small animal or application specific PET), it may be helpful to increase the above-described window ranges and isotope time differences (by as much as a factor of 10×). This can help increase the signal. A prompt gamma emitter is regarded as being any isotope that provides a time difference T between positron emission and prompt gamma emission as described above.

Low-count rate situations can arise where the tracer contrast is extremely high, or the volume of interest as compared to a human is very small. In cases where the contrast is high, then only small numbers of counts are needed to detect the accumulation of the radio tracer. In cases where the volume of interest is very small, then there are very few background processes. Because the background processes are not present, then the window ranges can be relaxed. These low-count situations can occur when attempting to image either small animals such as mice or chemical assays being conducted in small well plates.

Practice of the invention does not depend critically on the isotope that is used as the triple coincidence emitter. Any isotope that is consistent with the above-described principles can be employed. The prompt gamma emitter may emit more than one gamma ray at different energies. Also, there may be a plurality of prompt gamma rays that are emitted in the decay cascade. The prompt gamma ray energy or energies only need to differ from 511 keV (the positron annihilation energy). Multiple prompt gamma emitters can be employed. For example, in multi-isotope imaging there may be isotopes A, B and C present. In this example, A can be a clean positron emitter (i.e., no prompt gamma) and B and C can be triple coincident emitters where the energies of the prompt gamma rays from B and C are different and uniquely identifiable from each other.

Figure 6:
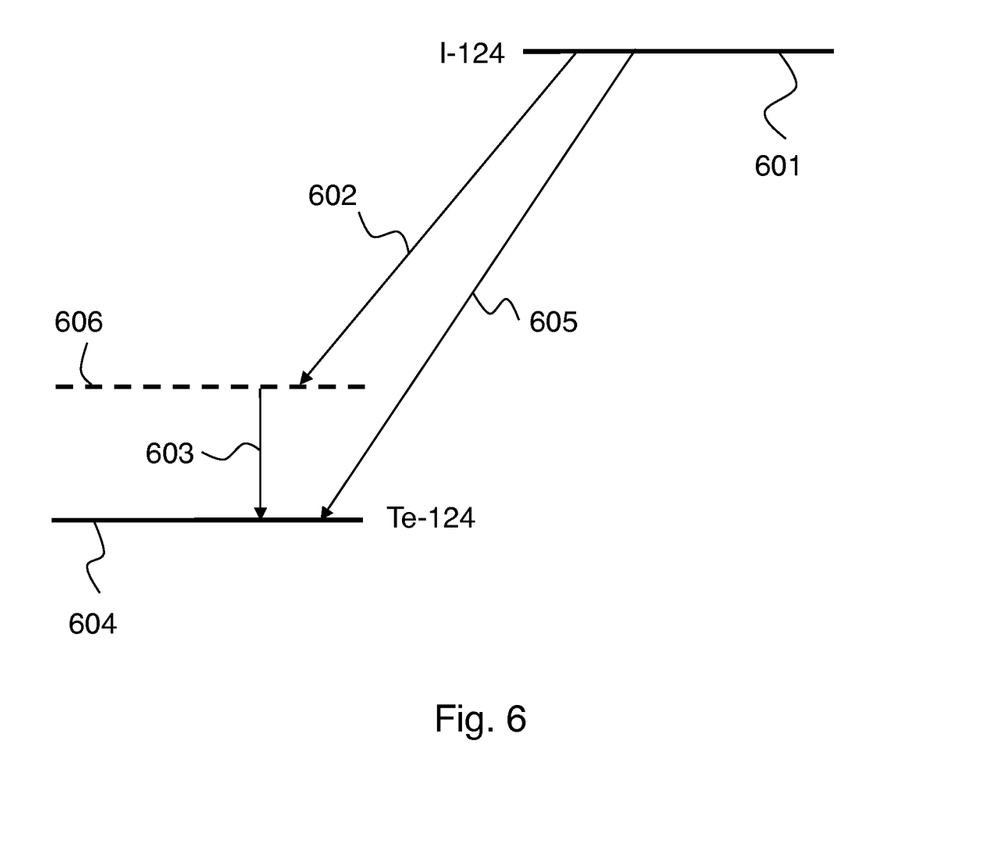
FIG. 6 is a simplified nuclear energy level diagram for I-124.

Suitable isotopes include, but are not limited to: Sc-44, I-124, Ga-68, Na-22 and In-110. FIG. 6 shows a simplified nuclear energy level diagram for the transition from I-124 to Te-124. Here energy level 601 is the parent positron emitting isotope (i.e., I-124). Energy level 604 is the stable daughter isotope (i.e., Te-124). Energy level 606 is an intermediate state that can be reached by radioactive decay from state 601, and which can decay to state 604 via a decay process 603 of gamma ray emission (this gamma ray energy is about 0.6 MeV).

Decay process 602 can occur in two ways—positron emission (11.7%) and electron capture (25.1%). Similarly, decay process 605 can also occur in two ways—positron emission (10.8%) and electron capture (24.1%). These probabilities do not add up to 100% because numerous other transitions are omitted from this figure for simplicity. Electron capture processes lead to emission of a gamma ray, but no positron is emitted.

In cases where decay process 602 is via positron emission, a prompt gamma can also be emitted via process 603. This is an example of the 3-photon events considered above. If I-124 decays via positron emission in process 605, there is no prompt gamma. Thus, some of the positron emissions from I-124 lead to 3-photon events, and others lead to 2-photon events. Calibration algorithms can be employed to correct for these different decay probabilities.

The invention claimed is:

1. A method of positron emission tomography (PET) comprising:
    labeling a first probe with a first positron emitting radionuclide to provide a first labeled probe, wherein the first probe is a selective probe that includes an antibody or ligand that is biologically responsive to receptor or antigen status;
    labeling a second probe with a second positron emitting radionuclide to provide a second labeled probe, wherein the second probe is a metabolic probe;
    wherein one of the first and second radionuclides provides double coincidence events in PET by emission of a positron, and the other of the first and second radionuclides provides triple coincidence events in PET by emission of a positron and a gamma ray photon;
    introducing the first and second labeled probes into an imaging subject simultaneously;
    performing PET on the imaging subject with a PET system capable of simultaneously providing double coincidence and triple coincidence PET images;
    wherein the PET system includes a detector that is responsive to the gamma ray photon, and is not responsive to photons generated by positron annihilation.

2. The method of claim 1, wherein the first probe selectively bonds to an antigen or receptor selected from the group consisting of: human epidermal growth factor receptor 2

(HER2/neu), estrogen receptor alpha (ER-α), estrogen receptor beta (ER-β), and prostate-specific membrane antigen (PSMA).

3. The method of claim 1, wherein the second probe is selected from the group consisting of: Fludeoxyglucose (FDG), 3'-fluoro-3'-deoxy-L-thymidine (FLT), and F-choline.

4. The method of claim 1, wherein the first positron emitting radionuclide provides double coincidence events in PET by emission of a positron, and wherein the second positron emitting radionuclide provides triple coincidence events in PET by emission of a positron and a gamma ray photon.

5. The method of claim 1, wherein the first positron emitting radionuclide provides triple coincidence events in PET by emission of a positron and a gamma ray photon, and wherein the second positron emitting radionuclide provides double coincidence events in PET by emission of a positron.

6. The method of claim 5, wherein the first positron emitting radionuclide comprises I-124, In-110, Sc-44, Ga-68, and Na-22.

7. The method of claim 5, wherein the second positron emitting radionuclide comprises F-18, C-11, or Cu-64.

8. The method of claim 1,
wherein the first probe is biologically responsive to an antigen or receptor that relates to a cancer.

9. The method of claim 8, wherein the cancer is selected from the group consisting of: breast cancer and prostate cancer.

\* \* \* \* \*